(12) United States Patent
Jeong et al.

(10) Patent No.: US 8,348,865 B2
(45) Date of Patent: Jan. 8, 2013

(54) NON-INTRUSIVE MOVEMENT MEASURING APPARATUS AND METHOD USING WEARABLE ELECTRO-CONDUCTIVE FIBER

(75) Inventors: Ji Wook Jeong, Daejeon (KR); Yong Won Jang, Daejeon (KR); Seung Hwan Kim, Daejeon (KR); Seon Hee Park, Daejeon (KR)

(73) Assignee: Electronics and Telecommunications Research Institute, Daejeon (KR)

( * ) Notice: Subject to any disclaimer, the term of this patent is extended or adjusted under 35 U.S.C. 154(b) by 767 days.

(21) Appl. No.: 12/539,969

(22) Filed: Aug. 12, 2009

(65) Prior Publication Data

US 2010/0137749 A1 Jun. 3, 2010

(30) Foreign Application Priority Data

Dec. 3, 2008 (KR) .................. 10-2008-0121854
Feb. 17, 2009 (KR) .................. 10-2009-0013051

(51) Int. Cl.
*A61B 5/103* (2006.01)
*A61B 5/117* (2006.01)

(52) U.S. Cl. ........................................ 600/595
(58) Field of Classification Search ................. 600/587, 600/595
See application file for complete search history.

(56) References Cited

U.S. PATENT DOCUMENTS 8,052,612 B2 * 11/2011 Tang et al. .................... 600/534
2007/0038057 A1 2/2007 Nam et al.
2008/0139969 A1 6/2008 Gough et al.

FOREIGN PATENT DOCUMENTS

| JP | 2007-533109 A | 11/2007 |
|---|---|---|
| KR | 1020010106838 A | 12/2001 |
| KR | 1020050052555 A | 6/2005 |
| KR | 1020060036965 A | 5/2006 |
| KR | 10-0759948 B1 | 9/2007 |
| KR | 10-0760594 B1 | 9/2007 |
| KR | 1020080071280 A | 8/2008 |
| WO | 2005/117030 A2 | 12/2005 |

* cited by examiner

*Primary Examiner* — Max Hindenburg
*Assistant Examiner* — Jonathan M Foreman
(74) *Attorney, Agent, or Firm* — Ladas & Parry LLP (57) ABSTRACT

There is provided a non-intrusive movement measuring apparatus and method using wearable electro-conductive fibers. A non-intrusive movement measuring apparatus using wearable electro-conductive fibers according to an aspect of the invention may include a signal measurement device measuring a plurality of movement signals using a plurality of electro-conductive fibers put on user's body parts and having resistances varying according to the volume of the user's body parts; a movement analysis device analyzing the plurality of movement signals to obtain a user's movement patterns and movement intensity; and a movement display device displaying a movement analysis result of the movement analysis device. Accordingly, user's movement can be measured without limiting the user's radius of action.

18 Claims, 8 Drawing Sheets

NON-INTRUSIVE MOVEMENT MEASURING APPARATUS AND METHOD USING WEARABLE ELECTRO-CONDUCTIVE FIBER

CROSS-REFERENCE TO RELATED APPLICATIONS

This application claims the priority of Korean Patent Application No. 2008-0121854 filed on Dec. 3, 2008 and Korean Patent Application No. 2009-0013051 filed on Feb. 17, 2009, in the Korean Intellectual Property Office, the disclosure of which is incorporated herein by reference.

BACKGROUND OF THE INVENTION

1. Field of the Invention

The present application relates to a movement measurement apparatus, and more particularly, to a non-intrusive movement measuring apparatus and method using wearable electro-conductive fibers that can measure a user's movements without limiting the user's radius of action.

2. Description of the Related Art

As many people's quality of life has been raised, public interest in health has been on the rise. In order for individuals to take care of and maintain their health, there has been an increasing demand to continuously measure a user's movements in order to analyze the intensity of exercise and the intensity of an activity.

To this end, movement measuring apparatuses using an electromyograph (EMG), a goniometer, an image analyzer or a force plate have been proposed.

An electromyograph using biological signals observes the state of muscles, causing a movement, that is, muscular activation rather than direct information about a change in joint angle. Unlike a goniometer or an image analyzer, the electromyograph is not suited for the accurate and constant measurement of changes in joint angle. Further, calculations are required to obtain useful information.

Since a goniometer is attached to the joints to analyze direct joint motions, the goniometer is the easiest, fastest and simplest method. However, since it is difficult to attach a goniometer to the body, continuous measurement is difficult to perform and freedom of movement is limited, thereby resulting in poor reproducibility.

An image analyzer is an expensive piece of equipment and is restricted by space. That is, a large space is required to install the image analyzer, and the image analyzer can only be used at a place where it is installed. In addition, many calculations are required to obtain movement analysis data from acquired image signals.

A shoe type force plate or pressure sensor is manufactured to measure pressure distribution while a user is walking. However, this device is only used to measure changes in pressure on the bottom of user's feet or a gait cycle, and it is difficult to obtain information about upper extremity movement or other body movements.

Electro-conductive fibers that combine fiber technologies and electronics have recently been under development. These electro-conductive fibers have electrical characteristics that vary according to the outside environment. Therefore, when electro-conductive fibers are woven into clothing, the clothes themselves are able to perform various electronic functions.

SUMMARY OF THE INVENTION

An aspect of the present application provides a non-intrusive movement measuring apparatus and method using wearable electro-conductive fibers that can measure a user's movements using electro-conductive fibers having resistances varying according to changes in the body part volume without limiting the user's radius of action.

According to an aspect of the present invention, there is provided a non-intrusive movement measuring apparatus using wearable electro-conductive fibers, the apparatus including: a signal measurement device measuring a plurality of movement signals using a plurality of electro-conductive fibers put on user's body parts and having resistances varying according to the volume of the user's body parts; a movement analysis device analyzing the plurality of movement signals to obtain a user's movement patterns and movement intensity; and a movement display device displaying a movement analysis result of the movement analysis device.

The plurality of electro-conductive fibers may be arranged on at least one of the user's body parts including cervical vertebral joints, left and right shoulder joints, left and right elbow joints, left and right wrist joints, left and right hip joints, left and right knee joints, left and right ankle joints, thorax, back, and abdomen.

Each of the plurality of electro-conductive fibers may be embodied as an attachment attachable to a user's skin or clothing.

Each of the plurality of electro-conductive fibers may be woven into clothing.

Each of the plurality of electro-conductive fibers may be arranged in a spiral fashion.

Each of the plurality of electro-conductive fibers may be arranged in a zigzag fashion.

The signal measurement device may include: a signal detection section outputting a plurality of analog signals having voltages corresponding to the respective resistances of the plurality of electro-conductive fibers; a signal conversion section performing amplification and filtration of the plurality of analog signals, and converting the analog signals into digital signals to generate a plurality of movement signals; and a signal transmission section transmitting the plurality of movement signals into the movement analysis device.

The signal detection section may include: a voltage supply unit supplying a driving voltage; and a plurality of voltage division units respectively corresponding to the plurality of electro-conductive fibers and varying voltage division ratios according to the corresponding resistances of the electro-conductive fibers so as to generate analog signals having voltages corresponding to the resistances of the corresponding electro-conductive fibers.

The signal measurement device may further include a detection signal display section displaying changes in the resistances of the plurality of electro-conductive fibers.

The movement analysis device may include: a signal reception section receiving the plurality of movement signals transmitted from the signal measurement device; a signal analysis section analyzing the plurality of movement signals to obtain the user's movement patterns and movement intensity; and a signal output section outputting an analysis result of the signal analysis section to the movement display device.

The signal analysis section may analyze the user's movement patterns and movement intensity to additionally calculate exercise intensity, activity intensity or calorie expenditure.

The movement display device may include: an image output section outputting an image corresponding to the analysis result of the signal analysis section; a sound output section outputting sound corresponding to the analysis result of the signal analysis section; and an external apparatus communication section connecting to a server on an external network and supplying information about the analysis result of the signal analysis section to the server.

The signal measurement device, the signal analysis device and the movement display device may communicate with each other through a wired, wireless or infrared connection.

According to another aspect of the present invention, there is provided a non-intrusive movement measuring method using wearable electro-conductive fibers, the method including: putting a plurality of electro-conductive fibers on user's body parts and measuring resistances of the plurality of electro-conductive fibers varying according to user movement; analyzing the resistances of the plurality of electro-conductive fibers to obtain a user's movement patterns and movement intensity; and notifying the user of the user's movement patterns and movement intensity.

The plurality of electro-conductive fibers may be arranged on at least one of the user's body parts including cervical vertebral joints, left and right shoulder joints, left and right elbow joints, left and right wrist joints, left and right hip joints, left and right knee joints, left and right ankle joints, thorax, back, and abdomen.

BRIEF DESCRIPTION OF THE DRAWINGS

The above and other aspects, features and other advantages of the present application will be more clearly understood from the following detailed description taken in conjunction with the accompanying drawings, in which.

DETAILED DESCRIPTION OF THE PREFERRED EMBODIMENT

Exemplary embodiments of the present application will now be described in detail with reference to the accompanying drawings. The invention may, however, be embodied in many different forms and should not be construed as limited to the embodiments set forth herein. Rather, these embodiments are provided so that this disclosure will be thorough and complete, and will fully convey the scope of the invention to those skilled in the art.

In the drawings, the shapes and dimensions may be exaggerated for clarity, and the same reference numerals will be used throughout to designate the same or like components.

In addition, unless explicitly described to the contrary, the word "comprise" and variations such as "comprises" or "comprising," will be understood to imply the inclusion of stated elements but not the exclusion of any other elements.

Figure 1:
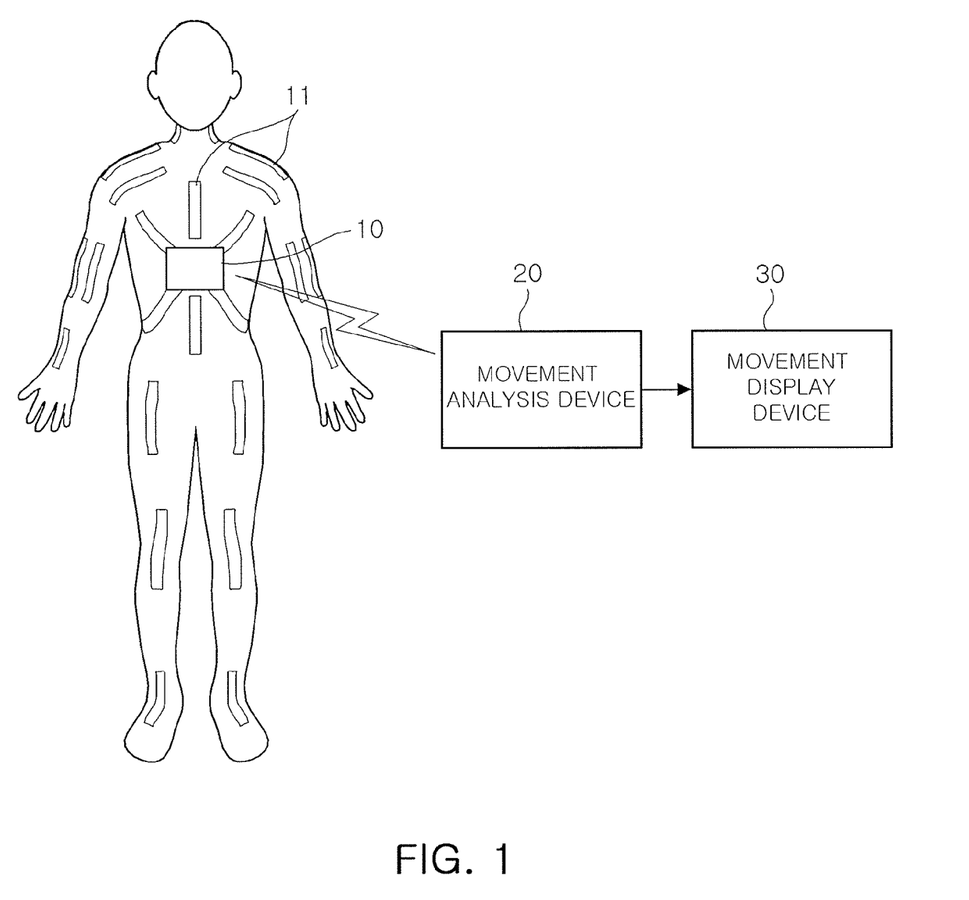
FIG. 1 is a conceptual view illustrating a non-intrusive movement measuring using wearable electro-conductive fibers apparatus according to an exemplary embodiment of the present invention.

FIG. 1 is a conceptual view illustrating a non-intrusive movement measuring apparatus using wearable electro-conductive fibers according to an exemplary embodiment of the invention.

Referring to FIG. 1, a non-intrusive movement measuring apparatus using wearable electro-conductive fibers according to this embodiment includes a signal measurement device 10, a movement analysis device 20 and a movement display device 30.

The signal measurement device 10 measures a plurality of movement signals using a plurality of electro-conductive fibers 11 that are put on a user's body and have resistances varying according to the volume of the user's body parts.

The movement analysis device 20 analyzes the plurality of movement signals to obtain a user's movement patterns and movement intensity.

The movement display device 30 displays a result of the movement analysis performed by the movement analysis device 20.

The electro-conductive fibers 11, shown in FIG. 1, generate resistances corresponding to the varying the volume of body parts. That is, changes in the volume of the user's body parts cause changes in the resistances of the electro-conductive fibers 11.

When the volume of the respective user's body parts is changed by a user's movement while the user's body is clothed with the electro-conductive fibers 11, the circumference (or length) of each of the electro-conductive fibers 11 changes, and thus the resistance of each of the electro-conductive fibers 11 changes correspondingly.

In this embodiment, taking advantage of the electrical characteristics of the electro-conductive fibers 11 having resistances varying according to the external environment, the user's body is clothed with the electro-conductive fibers 11, whereby movement signals containing information about a user's movement patterns and movement intensity are acquired.

Preferably, the electro-conductive fibers 11, shown in FIG. 1, are put on the user's body parts, especially where movement patterns and movement intensity can be most efficiently measured in terms of anatomy.

Figure 2:
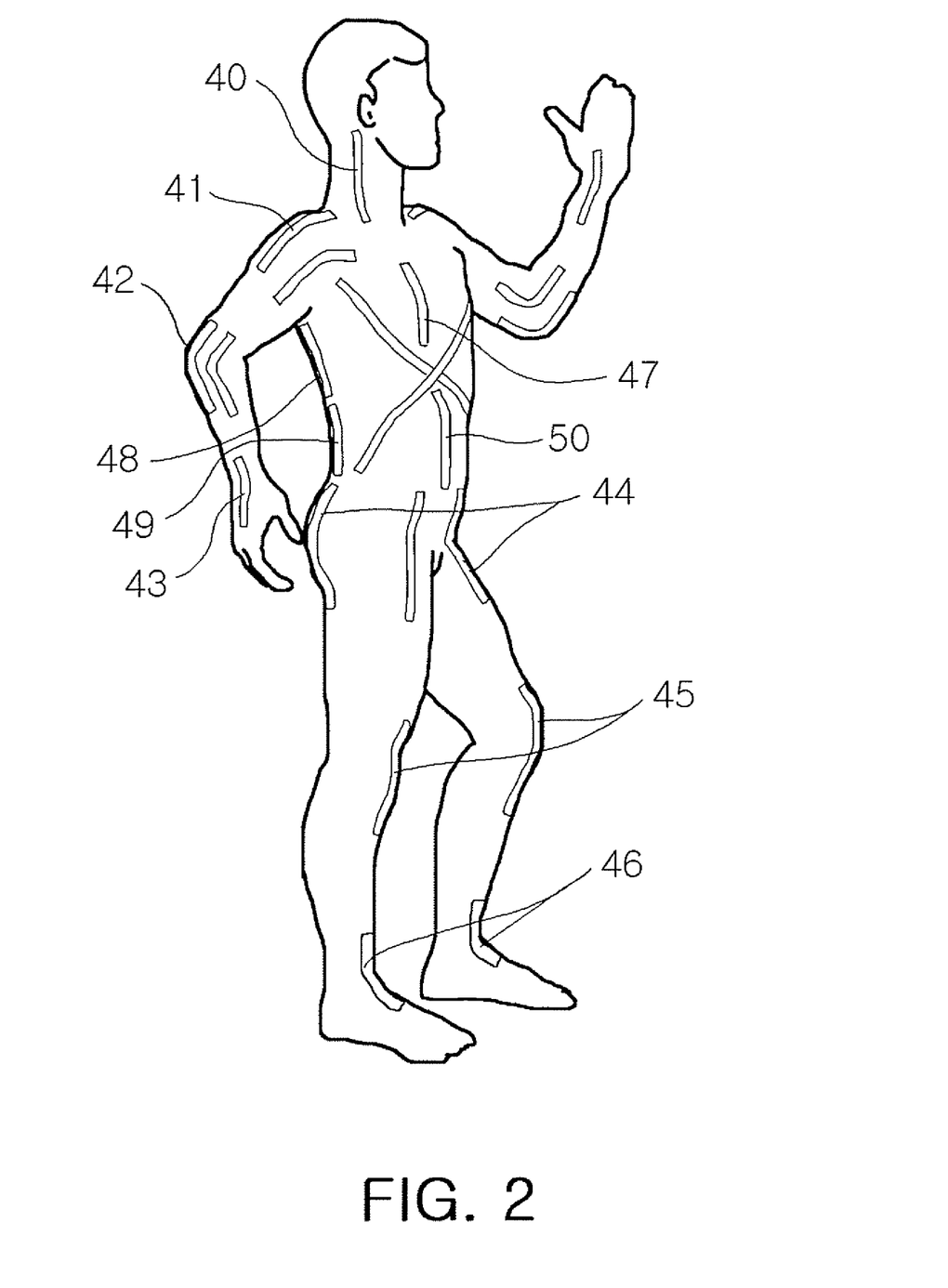
FIG. 2 is a view illustrating an example of how electro-conductive fibers are put on the user's body parts according to an exemplary embodiment of the present invention.

FIG. 2 is a view illustrating an example of how electro-conductive fibers are put on the user's body parts according to an exemplary embodiment of the present invention In this embodiment, the joints, the thorax, the back and the abdomen of the human body are set to movement measurement reference points on the basis of the fact that if a person moves, the angles of the user's body parts change and the volume of the corresponding body parts changes correspondingly.

Herein, movement measurement reference points are set to at least one of the user's body parts including cervical vertebral joints 40, left and right shoulder joints 41, left and right elbow joints 42, left and right wrist joints 43, left and right hip joints 44, left and right knee joints 45, left and right ankle joints 46, thorax 47, back 48 and 49, and abdomen 50. Then, electro-conductive fibers are put on the corresponding user's body parts.

Figure 3A:
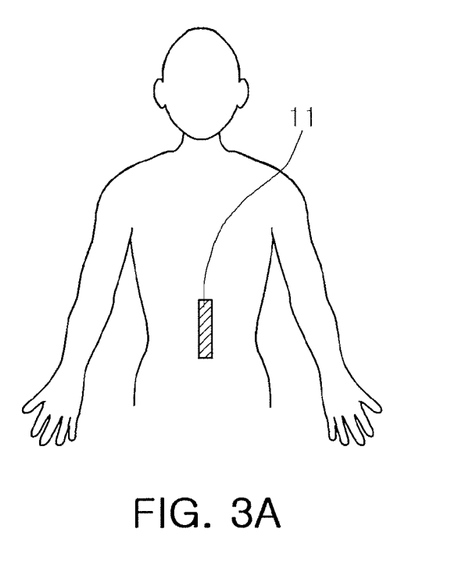
FIGS. 3A and 3B are views illustrating embodied examples of electro-conductive fibers according to an exemplary embodiment of the present invention.
Figure 3B:
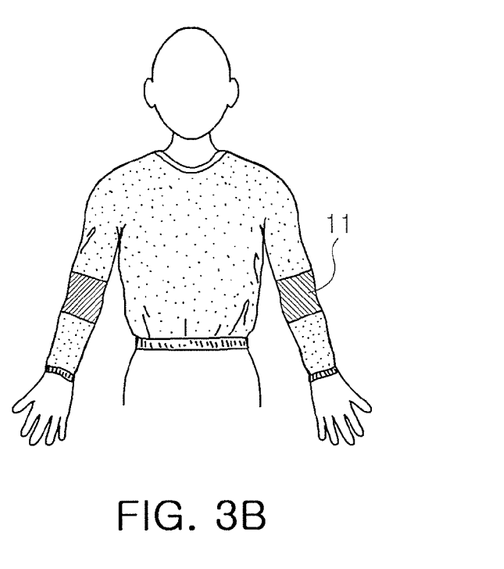

As shown in FIG. 3A, the electro-conductive fibers 11 may be embodied as an attachment that can be attached to a user's skin or clothing. Alternatively, as shown in FIG. 3B, the electro-conductive fibers 11 may be woven into clothing.

Figure 4A:
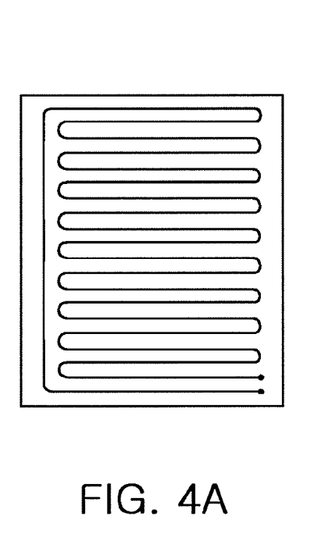
FIGS. 4A and 4B are views illustrating arrangement examples of electro-conductive fibers according to an exemplary embodiment of the present invention.
Figure 4B:
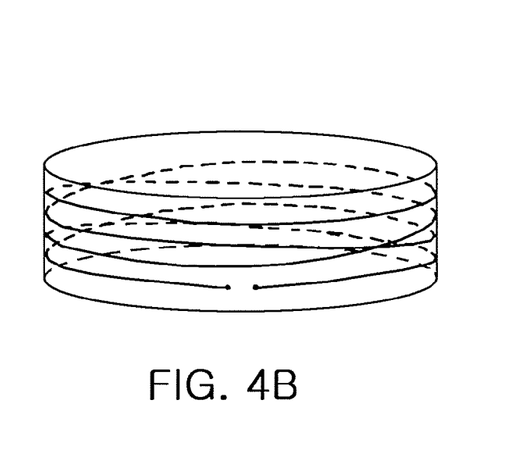

The arrangement of the electro-conductive fibers 11 may vary according to how the electro-conductive fibers 11 are embodied. For example, shown in FIG. 4A, when the electro-conductive fibers 11 are realized as an attachment, the electro-conductive fibers 11 may be arranged in a zigzag fashion. Alternatively, as shown in FIG. 4B, when the electro-conductive fibers 11 are woven into clothing, the electro-conductive fibers 11 may be arranged in a spiral fashion.

The zigzag or spiral arrangement of the electro-conductive fibers 11 increases the contact area between the electro-conductive fibers 11 and the user's body to thereby maximize the effect of resistance variation according to user's movement.

Figure 5:
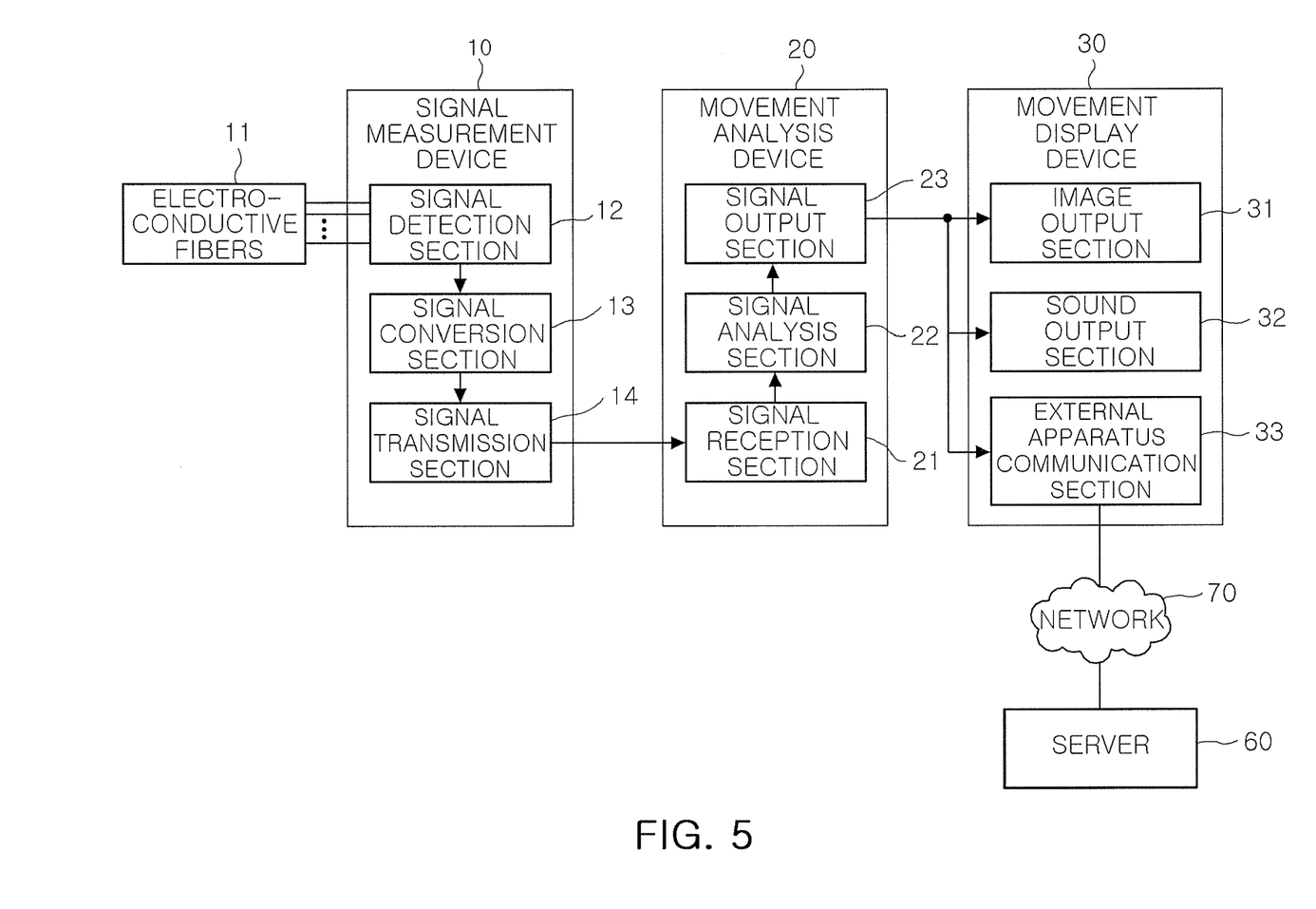
FIG. 5 is a detailed configuration view illustrating a non-intrusive movement measuring apparatus using wearable electro-conductive fibers according to an exemplary embodiment of the present invention.

FIG. 5 is a detailed configuration view illustrating a non-intrusive movement measuring apparatus using electro-conductive fibers according to an exemplary embodiment of the invention.

Referring to FIG. 5, the signal measurement device 10 includes the plurality of electro-conductive fibers 11, a signal detection section 12, a signal conversion section 13 and a signal transmission section 14; the movement analysis device 20 includes a signal reception section 21, a signal analysis section 22, a signal output section 23; and the movement display device 30 includes an image output section 31, a sound output section 32, and an external apparatus communication section 33.

Hereinafter, the functions of the respective components will be described.

As described above, the plurality of electro-conductive fibers 11 are distributed and put on movement measurement reference points. Each of the electro-conductive fibers 11 generates a resistance corresponding to the volume (or a change in the circumference) of the corresponding user's body part where the electro-conductive fiber 11 is located.

That is, when the volume of the movement measurement reference points, such as the joints, the thorax, the back and the abdomen of the human body, changes due to a user's movement, the corresponding resistance of each of the plurality of electro-conductive fibers 11 changes correspondingly.

The signal detection section 12 detects the resistances of the plurality of electro-conductive fibers 11 and generates and outputs a plurality of analog signals having voltages corresponding to the detected resistances.

Figure 6:
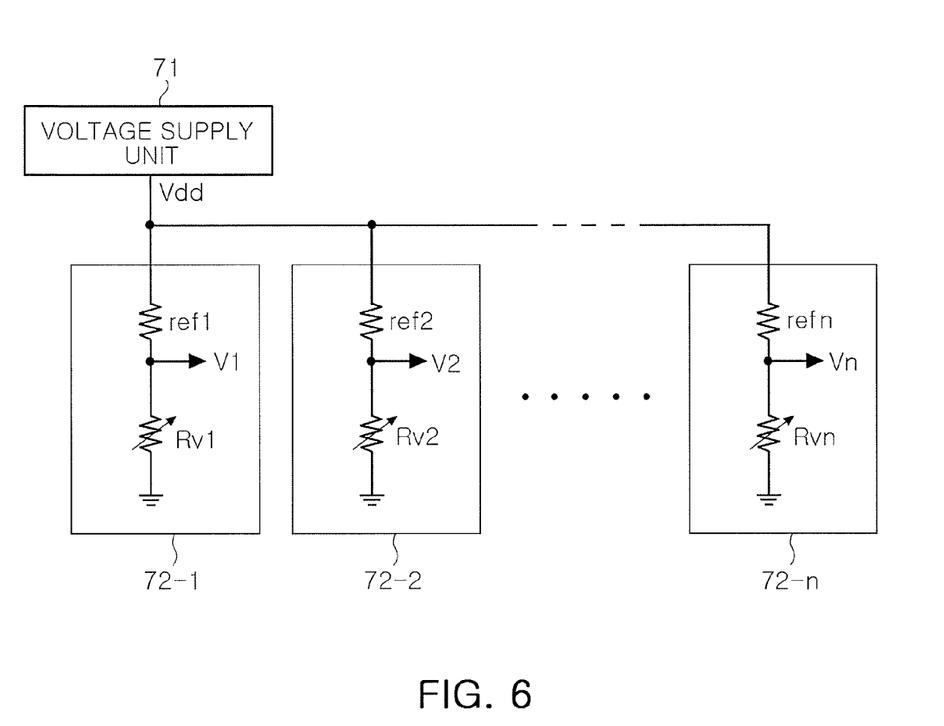
FIG. 6 is a detailed configuration view illustrating a signal detection section according to an exemplary embodiment of the present invention.

Preferably, as shown in FIG. 6, the signal detection section 12 includes a voltage supply unit 71 that supplies a driving voltage Vdd and a plurality of voltage division units 72-1 to 72-$n$ that vary a voltage division ratio with respect to the driving voltage Vdd according to the respective resistances of the electro-conductive fibers 11. Each of the voltage division units, for example, the voltage division unit 72-1 includes a reference resistor Rref1 connected in series with a driving voltage Vdd terminal and a variable resistor Rv1, which is realized as the electro-conductive fiber 11.

When the resistance of the electro-conductive fiber 11, put on the corresponding user's body part, changes due to the volume of the corresponding body part that is caused by a user's movement, the signal detection section 12 outputs an analog signal having a voltage value V1 corresponding to the changed resistance through the voltage division unit 72-1 having the electro-conductive fiber 11 as a variable resistor.

As such, the signal detection section 12 detects the resistances of the electro-conductive fibers 11 that correspond to the volume of the user's body parts that vary according to the user's movement. Then, the signal detection section 12 further varies the voltage values of the analog signals.

The signal conversion section 13 amplifies the voltage of each of the plurality of analog signals, transmitted from the signal detection section 12, filters noise, converts the analog signals into digital signals, and generates movement signals. The signal conversion section 13 adds information about a signal detection position to the movement signals, which are then transmitted to the signal transmission section 14.

The signal transmission section 14 communicates with the movement analysis device 20 through a wired, wireless or infrared connection, and supplies the plurality of movement signals, output from the signal conversion section 13, to the movement analysis device 20.

The signal reception section 21 of the movement analysis device 20 communicates with the signal transmission section 14 of the signal measurement device 10 through a wired, wireless or infrared connection, and receives a plurality of movement signals output from the signal conversion section 13.

The signal analysis section 22 has a signal analysis reference that defines a resistance change pattern based on the user's movement patterns and movement intensity (for example, angle change or twisting degree) and analyzes the plurality of movement signals according to the signal analysis reference to thereby obtain a user's movement patterns and movement intensity.

In general, repetitive movements of the joints and the particular user's body parts, such as folding, bending, twisting, and straightening, caused by the user's movement lead to a periodic change in the resistances of the electro-conductive fibers 11. Types of movements are limited according to which user's body parts the electro-conductive fibers 11 are attached to. That is, a repetition period of measurement variation and an amplitude between repeated maximum-minimum measurements are also be converted into predetermined patterns according to the user's movement patterns and movement intensity. Thus, in this embodiment, a resistance change pattern based on movement patterns and the intensity of a movement is previously defined, and a plurality of movement signals are analyzed using the resistance change pattern, thereby analyzing movement patterns and movement intensity.

The signal analysis section 22 further includes an additional information calculation reference and analyzes movement patterns and the intensity of a movement according to the additional information computation reference to thereby additionally calculate exercise intensity, activity intensity or calorie expenditure.

The signal analysis section 22 may additionally calculate activity intensity or calorie expenditure from the movement patterns and the movement intensity on the basis of an additional information computation algorithm and statistical information. That is, a conversion formula (or dynamic information) is proposed by which speed and intensity according to a type of movement can be obtained using the movement patterns and the movement intensity. Estimation values of the activity intensity and calorie expenditure can be obtained using the conversion formula.

The signal output section 23 communicates with the movement display device 30 though a wired, wireless or infrared connection. The signal output section 23 generates image and sound information so that the user understands a result of the movement analysis of the movement analysis device 20 in an audiovisual way, and supplies the generated image and sound information to the movement display device 30.

The image output section 31 displays an image corresponding to the analysis result of the signal analysis section 22 on a screen. The sound output section 32 outputs sound corresponding to the analysis result of the signal analysis section 22 through a speaker.

The external apparatus communication section 33 connects to a server 60 through an external network 70 and supplies movement analysis information, being currently obtained, to the server 60.

In this way, the movement display device 30 according to this embodiment can notify a user of the movement analysis result both in the case of a who user is distant from the movement measuring apparatus and in the case of a user who is adjacent to the movement measuring apparatus.

The description has been made of a case in which the movement analysis device 20 and the movement display device 30 are separated from each other. However, in a case of an actual application, the movement analysis device 20 and the movement display device 30 may form a single body.

Figure 7:
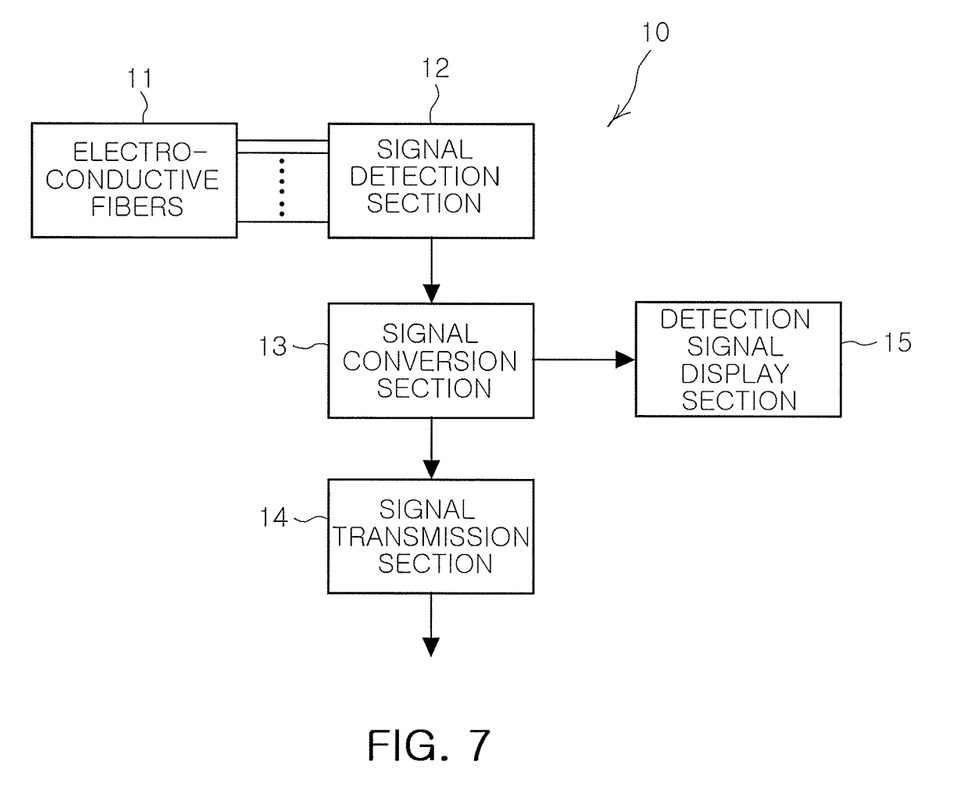
FIG. 7 is a configuration view illustrating a signal measurement device according to an exemplary embodiment of the present invention.

As shown in FIG. 7, the signal measurement device 10 further includes a detection signal display section 15 that displays an output signal of the signal conversion section 13 so that the signal measurement device 10 can directly inform a user of changes in the resistances of the plurality of electro-conductive fibers 11 caused by a change in a user's posture, that is, a user's movement.

Figure 8:
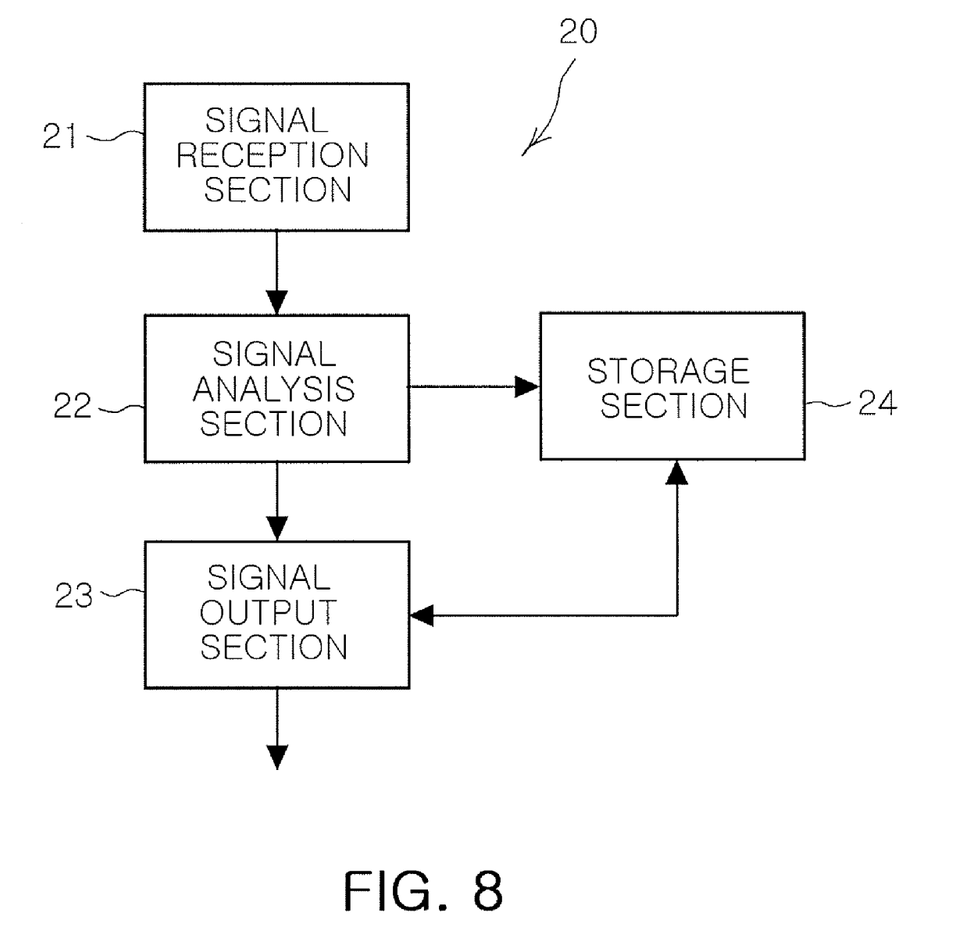
FIG. 8 is a configuration view illustrating a movement analysis device according to an exemplary embodiment of the present invention.

As shown in FIG. 8, the movement analysis device 20 further includes a storage section 24, serving as a memory, in which the currently obtained analysis result is stored. Therefore, the storage section 24 allows the analysis result to be searched and measured later.

Figure 9:
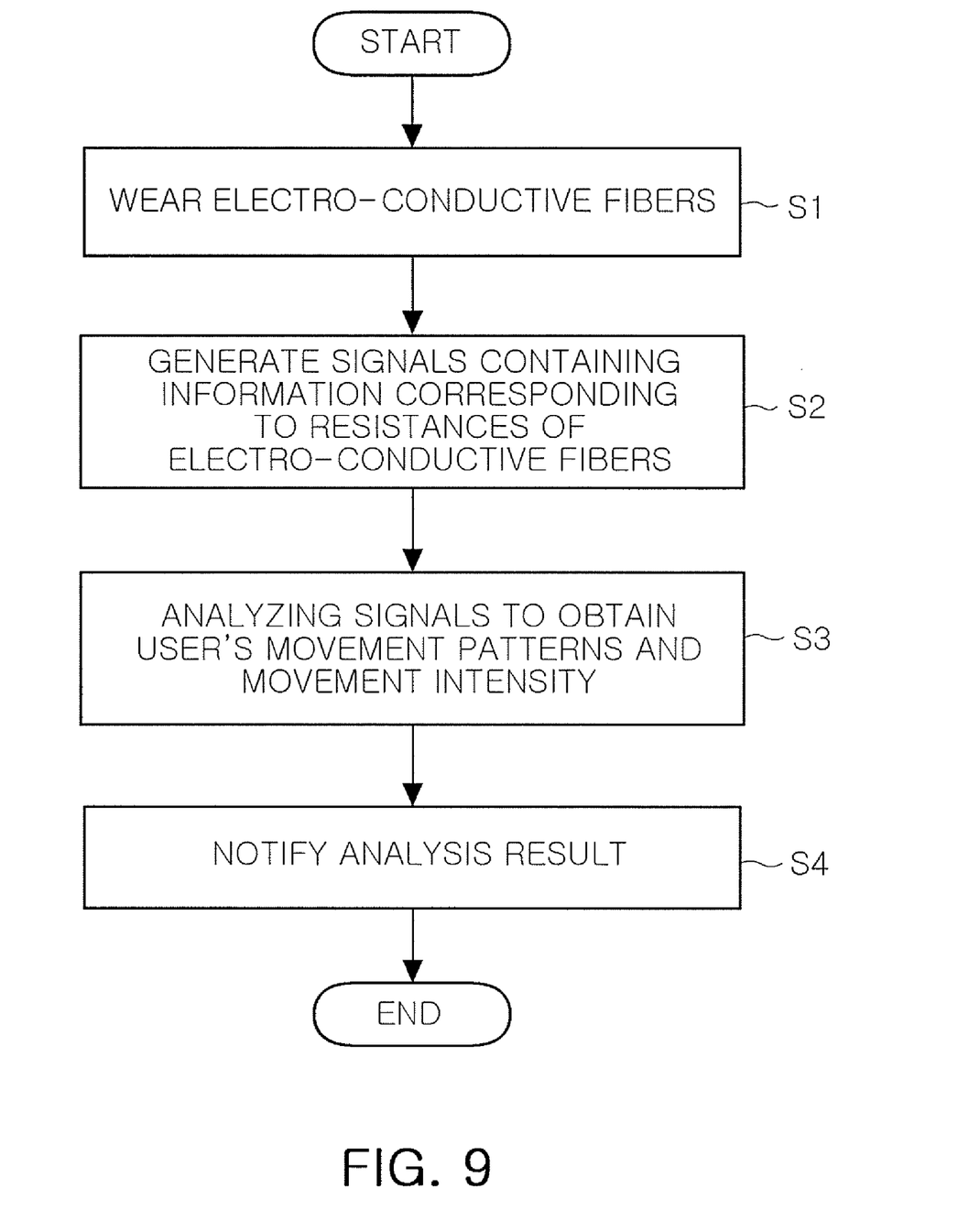
FIG. 9 is a flow chart illustrating the operation of a non-intrusive movement measuring method using electro-conductive fibers according to an exemplary embodiment of the present invention.

FIG. 9 is a flow chart illustrating the operation of a non-intrusive movement measuring apparatus using electro-conductive fibers according to an exemplary embodiment of the invention.

First, as shown in FIG. 2, a user wears the plurality of electro-conductive fibers 11 on reference points in consideration of movement characteristics to be detected in operation S1.

Then, the resistances of the plurality of electro-conductive fibers 11 vary according to the volume (or changes in circumference) of the user's body parts caused by a change in user's posture, that is, a user's movement. The signal measurement device 10 generates a plurality of signals containing corresponding information in operation S2.

The movement analysis device 20 analyzes the plurality of signals, generated in operation S2, according to a signal analysis reference, and obtains a user's movement patterns and movement intensity. The movement analysis device 20 additionally calculates exercise intensity, activity intensity or calorie expenditure from the movement patterns and the movement intensity according to an additional information calculation reference in operation S3.

The movement display device 30 checks a current display mode and then outputs a result of the analysis, obtained in operation S3, in the form of an image or sound through a screen or a speaker, or supplies the analysis result to the server 60 on the external network 70 in operation S4.

As set forth above, according to exemplary embodiments of the invention, a non-intrusive movement measuring apparatus and method using wearable electro-conductive fibers can easily measure user's movement without limiting the user's radius of action.

Further, a non-intrusive movement measuring apparatus and method using wearable electro-conductive fibers according to an exemplary embodiment uses electro-conductive fibers having resistances varying according to changes in the body part volume without applying additional currents to the user's body so as to measure movement. Accordingly, user's movements can be measured more safely.

While the present application has been shown and described in connection with the exemplary embodiments, it will be apparent to those skilled in the art that modifications and variations can be made without departing from the spirit and scope of the invention as defined by the appended claims.

What is claimed is:

1. A non-intrusive movement measuring apparatus comprising:
    a plurality of electro-conductive fibers configured to exhibit variable resistances when the electro-conductive fibers are folded, bent, twisted, and straightened;
    a signal measurement device coupled to the electro-conductive fibers and configured to measure a plurality of movement signals from the electro-conductive fibers such that the movement signals corresponding to the variable resistances of the electro-conductive fibers, wherein the signal measurement device comprises:
        a signal detection section configured to output analog voltage signals that correspond to the variable resistances of the electro-conductive fibers;
        a signal conversion section configured to amplify, filter and convert digitally the analog voltage signals into movement signals; and
        a signal transmission section configured to transmit the movement signals to a movement analysis device;
    the movement analysis device configured to analyze the movement signals and configured to obtain movement patterns and movement intensity of the electro-conductive fibers; and
    a movement display device configured to display a movement analysis result from the movement analysis device.

2. The apparatus of claim 1, wherein the electro-conductive fibers are attachable to a user's skin or clothing.

3. The apparatus of claim 1, wherein the electro-conductive fibers are woven into clothing.

4. The apparatus of claim 1, wherein the electro-conductive fibers are arranged in a spiral fashion.

5. The apparatus of claim 1, wherein the electro-conductive fibers are arranged in a zigzag fashion.

6. The apparatus of claim 1, wherein the movement display device comprises:
    an image output section configured to output an image that corresponds to the analysis result of the signal analysis section;
    a sound output section configured to output sound that corresponds to the analysis result of the signal analysis section; and
    an external apparatus communication section configured to connect to a server on an external network and configured to supply information about the analysis result of the signal analysis section to the server.

7. The apparatus of claim 1, wherein the signal detection section comprises:
    a voltage supply unit configured to supply a driving voltage; and
    a plurality of voltage division units configured to vary voltage division ratios in accordance to the variable resistances of the electro-conductive fibers so as to generate the analog voltage signals that correspond to the variable resistances of the electro-conductive fibers.

8. The apparatus of claim 1, wherein the signal measurement device further comprises a detection signal display section configured to display changes in the variable resistances of the electro-conductive fibers.

9. The apparatus of claim 1, wherein the movement analysis device comprises:
a signal reception section configured to receive the movement signals transmitted from the signal measurement device;
a signal analysis section configured to analyze the movement signals to obtain movement patterns and movement intensity of the electro-conductive fibers; and
a signal output section configured to output an analysis result of the signal analysis section to the movement display device.

10. The apparatus of claim 9, wherein the signal analysis section further comprises a signal analysis reference, and is configured to analyze the movement patterns and movement intensity based on the signal analysis reference to additionally calculate exercise intensity, activity intensity or calorie expenditure.

11. The apparatus of claim 1, wherein the signal measurement device, the signal analysis device and the movement display device are configured to communicate with each other through a wired, wireless or infrared connection.

12. A non-intrusive movement measuring apparatus comprising:
a plurality of electro-conductive fibers configured to exhibit variable resistances when the electro-conductive fibers are folded, bent, twisted, and straightened;
a signal measurement device coupled to the electro-conductive fibers and configured to measure a plurality of movement signals from the electro-conductive fibers such that the movement signals corresponding to the variable resistances of the electro-conductive fibers;
the movement analysis device configured to analyze the movement signals and configured to obtain movement patterns and movement intensity of the electro-conductive fibers; and
a movement display device configured to display a movement analysis result from the movement analysis device, wherein the movement display device comprises:
an image output section configured to output an image that corresponds to the analysis result of the signal analysis section;
a sound output section configured to output sound that corresponds to the analysis result of the signal analysis section; and
an external apparatus communication section configured to connect to a server on an external network and configured to supply information about the analysis result of the signal analysis section to the server.

13. The apparatus of claim 12, wherein the signal measurement device comprises:
a signal detection section configured to output analog voltage signals that correspond to the variable resistances of the electro-conductive fibers;
a signal conversion section configured to amplify, filter and digitally convert the analog voltage signals into movement signals; and
a signal transmission section configured to transmit the movement signals to a movement analysis device.

14. The apparatus of claim 13, wherein the signal detection section comprises:
a voltage supply unit configured to supply a driving voltage; and
a plurality of voltage division units configured to vary voltage division ratios in accordance to the variable resistances of the electro-conductive fibers so as to generate the analog voltage signals that correspond to the variable resistances of the electro-conductive fibers.

15. The apparatus of claim 12, wherein the movement analysis device further comprises:
a signal reception section configured to receive the movement signals transmitted from the signal measurement device;
a signal analysis section configured to analyze the movement signals to obtain movement patterns and movement intensity of the electro-conductive fibers; and
a signal output section configured to output an analysis result of the signal analysis section to the movement display device.

16. The apparatus of claim 15, wherein the signal analysis section further comprises a signal analysis reference, and is configured to analyze the movement patterns and movement intensity based on the signal analysis reference to additionally calculate exercise intensity, activity intensity or calorie expenditure.

17. A non-intrusive movement measuring method using wearable electro-conductive fibers, the method comprising:
putting the electro-conductive fibers on a user's body parts;
measuring a plurality of movement signals such that the movement signals corresponding to variable resistances of the electro-conductive fibers;
outputting analog voltage signals that correspond to the variable resistances of the electro-conductive fibers;
amplifying, filtering and digitally converting the analog voltage signals into movement signals;
transmitting the movement signals to a movement analysis device;
analyzing the movement signals to obtain movement patterns and movement intensity of the electro-conductive fibers on the user's body; and
displaying a movement analysis result from the movement analysis device; and
notifying the user of the movement patterns and movement intensity.

18. The method of claim 17, wherein the electro-conductive fibers are arranged on at least one of the user's body parts comprising cervical vertebral joints, left and right shoulder joints, left and right elbow joints, left and right wrist joints, left and right hip joints, left and right knee joints, left and right ankle joints, thorax, back, and abdomen.

* * * * *